(12) United States Patent
Coury et al.

(10) Patent No.: US 7,096,865 B1
(45) Date of Patent: Aug. 29, 2006

(54) PERSONAL GAS SUPPLY DELIVERY SYSTEM

(75) Inventors: Joseph E. Coury, Lakewood, OH (US); John S. Massaad, Lakewood, OH (US)

(73) Assignee: Oxygen Lifeline, LLC, Brecksville, OH (US)

( * ) Notice: Subject to any disclaimer, the term of this patent is extended or adjusted under 35 U.S.C. 154(b) by 815 days.

(21) Appl. No.: 09/691,713

(22) Filed: Oct. 18, 2000

(51) Int. Cl.
*A61M 15/00* (2006.01)
*H05B 3/00* (2006.01)
*A62B 7/00* (2006.01)
*A62B 9/00* (2006.01)

(52) U.S. Cl. .............. 128/203.17; 128/200.11; 128/202.22; 128/203.27; 128/205.23; 261/DIG. 65

(58) Field of Classification Search ........... 128/200.11, 128/201.13, 203.16, 203.17, 203.26, 203.27, 128/202.22, 205.23, 203.14, 204.17, 205.12; 261/154, 130, 104, 107, DIG. 65, 203.14, 261/204.17, 205.12
See application file for complete search history.

(56) References Cited

U.S. PATENT DOCUMENTS

| | | | |
|---|---|---|---|
| 3,133,997 A | 5/1964 | Greene | 200/83 R |
| 3,789,837 A * | 2/1974 | Philips et al. | 128/145.8 |
| 3,794,026 A * | 2/1974 | Jacobs | 128/145.8 |
| 3,831,595 A * | 8/1974 | Valenta et al. | 128/145.8 |
| 3,985,131 A * | 10/1976 | Buck et al. | 128/145.8 |
| 4,381,774 A * | 5/1983 | Schreiber et al. | 128/202.22 |
| 4,674,321 A | 6/1987 | Joshi | 73/40.7 |
| 4,681,099 A * | 7/1987 | Sato et al. | 128/204.23 |
| 4,821,709 A * | 4/1989 | Jensen | 128/204.21 |
| 5,057,822 A | 10/1991 | Hoffman | 340/611 |
| 5,165,398 A * | 11/1992 | Bird | 128/204.25 |
| 5,293,866 A | 3/1994 | Padula | 128/204.18 |
| 5,347,843 A * | 9/1994 | Orr et al. | 73/3 |
| 5,423,313 A * | 6/1995 | Olsson et al. | 128/204.21 |
| 5,452,714 A * | 9/1995 | Anderson et al. | 128/205.11 |
| 5,457,333 A | 10/1995 | Fukui | 257/253 |
| 5,534,851 A * | 7/1996 | Russek | 128/202.22 |
| 5,540,220 A * | 7/1996 | Gropper et al. | 128/204.23 |
| 5,868,133 A * | 2/1999 | DeVries et al. | 128/204.18 |
| 5,881,717 A * | 3/1999 | Isaza | 128/202.22 |
| 5,890,490 A * | 4/1999 | Aylsworth et al. | 128/203.12 |
| 6,062,216 A * | 5/2000 | Corn | 128/204.23 |
| 6,067,022 A | 5/2000 | Laswick et al. | 340/626 |
| 6,098,617 A * | 8/2000 | Connell | 128/200.26 |

OTHER PUBLICATIONS

MPL publication mpl@pressureswitch.com 555 SW 12 th Avenue Pompano Beach, Florida 33069.

* cited by examiner

*Primary Examiner*—Henry Bennett
*Assistant Examiner*—Andrea M. Ragonese
(74) *Attorney, Agent, or Firm*—Forrest L. Collins Law Offices, LLC; Forrest L. Collins

(57) ABSTRACT

A supply of gas such as oxygen is provided to a person in need of such gas supply. The delivery system includes an alarm to alert the recipient of the gas or another when and if the gas supply is disrupted. The alarm system preferably includes a reset and on-off switch that is recessed sufficiently to prevent accidental disabling of the alarm system.

4 Claims, 3 Drawing Sheets

PERSONAL GAS SUPPLY DELIVERY SYSTEM

BACKGROUND OF THE INVENTION

1. Field of the Invention

The purpose of this invention is to employ a gas flow alarm in a personal gas supply delivery system 2. Description of the Art Practices Hospitals, nursing homes, dental offices, clinics and a number of other health care institutions utilize medical gasses in rendering care to patients. It is well known to administer oxygen, air, and nitrous oxide to patients for treatment of a variety of different conditions or during surgical operations.

A number of medical institutions now employ medical gas systems which use a central gas supply source for providing a positive flow of medical gasses. These systems often utilize a network of conduits or supply lines to deliver the medical gas remote from the central source of the medical gas. The networks often include main and branch shut-off valves to enable isolation of a portion of the network in the event of damage or fire, or to effect needed repairs.

The lives of patients may depend on receiving a reliable source of the medical gas, a real need has developed to ensure that the medical gas system is functioning properly, and to annunciate an alarm in the event a malfunction or alarm condition is detected. Such conditions may occur, for example, when the shut-off valve is either partially or fully closed. In such circumstances, the necessary supply of gas may be insufficient or non-existent.

A further inadvertent interruption of the medical gas supply may occur when the medical gas is humidified. Commonly employed humidifying systems utilize a threaded plastic vessel that is screwed into a threaded plastic cap. If the threads of the threaded plastic vessel or threaded plastic cap are damaged or misaligned the medical gas may be lost to the surrounding environment with the consequent non-delivery of the medical gas to the patient.

There is a further need to detect other defects in the system that may impair the medical gas system effectiveness. For example, usage of the system may eventually result in low pressure conditions in the supply tank when the supply of gas is nearly exhausted. There is a further need for early detection of these problems so that replacement sources of medical gas may be provided to the patient before the medical gas delivery system becomes completely inoperative.

Finally, due to the escalating costs associated with medical care and the shortage of trained nurses and technicians, monitoring of the medical gas delivery systems should be easy and capable of instant recognition of system faults. In particular, the recipient of the medical gas or a visitor of the patient should be able to recognize system faults.

Several methods using various apparatus have been employed to determine if a supply of a gas is within operating parameters. Such methods and aparrati are disclosed below.

U.S. Pat. No. 6,067,022 granted to Laswick, et al., on May 23, 2000 describes an in-line low supply pressure alarm device powered solely by supply flow of pressurized gas from a gas supply for providing an alarm signal when supply gas pressure is below a selected minimum pressure. The alarm device includes a manifold having an input port for communicating with the supply gas supply, an output port for conducting the gas downstream and a manifold chamber disposed therebetween.

The Laswick, et al., patent utilizes gas powered alarms such as an audible reed alarm or a visual pneumatic alarm are connected to the manifold chamber via an alarm supply conduit, and produce an alarm signal when pressurized gas passes to the alarms. According to the Laswick, et al., patent a supply gas pressure sensor, in communication with the manifold chamber, produces an actuating flow of pressurized gas by activating a pressure switch, in response to sensing of an supply gas pressure below the selected minimum pressure.

U.S. Pat. No. 6,067,022 to Laswick, et al., further provides a pneumatic alarm output switch, in the alarm supply conduit and in communication with the pressure sensor and pressure switch via an actuation conduit, controls gas flow to the alarms in response to the actuating flow. The Laswick, et al., patent preferably includes an alarm oscillation system is included for alternating the direction of the actuating flow to and from the alarm output switch, to open and close the alarm output switch thereby turning the alarm on and off in a cyclical fashion.

U.S. Pat. No. 4,674,321 issued to Joshi on Jun. 23, 1987 describes a leak detector employing an ion-conducting membrane is disclosed. The Joshi patent describes an oxygen-ion conducting membrane which employs a high vacuum on one side is used to detect very small quantities of oxygen flowing through a minute fissure in a part to be tested for leaks. The Joshi patent further describes an oxygen-ion conducting membrane which is biased with direct current voltage to drive oxygen-ions through the membrane away from the high vacuum side.

U.S. Pat. No. 3,133,997 to Greene issued May 19, 1964 describes a fluid-pressure activated switch. Pressure activated switches are described in the MPL publication available at mpl@pressureswitch.com 555 SW 12 th Avenue Pompano Beach, Fla. 33069. Further disclosures of pressure activated switches are found at World Magnetics 810 Hastings Street Traverse City, Mich. 49686, telephone: 231-946-3800 and fax: 231-946-0274 and located on the web at http://www.worldmagnetics.com.

U.S. Pat. No. 5,057,822 to Hoffman issued Oct. 15, 1991 describes a medical gas alarm system is provided which includes a sensor unit pneumatically connected to a medical gas supply line and a switch connected to a valve in the supply line for detecting the open condition of the valve.

In the Hoffman patent, in the event either the sensor detects a high pressure or low pressure condition in the supply line or closing of the valve activates the switch, an alarm signal is received by an alarm module and an alarm is activated. The alarm of the Hoffman patent may be visual, audible or both. During normal operations, the alarm module of the Hoffman patent displays both a system on condition and a digital display indicating the pressure in the supply line.

The Hoffman patent also includes a method of monitoring the condition of a medical gas delivery system which includes sensing the pressure in the gas supply line, detecting the open condition of the valve, transmitting an alarm signal to an alarm module in response to alarm conditions detected either as a result of improper pressure or valve closure, and generating a humanly perceptible alarm warning in response to receipt of an alarm signal.

Fukui in U.S. Pat. No. 5,457,333 issued Oct. 10, 1995 describes a gas sensor comprises a precious metal electrode, a semiconductor layer entirely or partly covering the precious metal electrode, a barrier layer having a high potential formed at an interface between the precious metal electrode and the semiconductor layer. The Fukui patent recites a gas sensor for use in a leak detector for detecting a fuel gas such as town gas, the sensor comprising a precious metal electrode; and a semiconductor layer at least partly covering said precious metal electrode, wherein the semiconductor layer includes, as a main component, at least one substance selected from the group consisting of tin oxide, zinc oxide and indium oxide. The Fukui patent precious metal electrode is formed of a substance selected from the group consisting of platinum, gold, ruthenium, lead, silver, iridium, and alloys thereof and has a barrier layer having a high potential formed between said precious metal electrode and said semiconductor layer and on a surface of said precious metal electrode. The barrier layer described in the Fukui patent comprises either a substance formed by electrodeposition and selected from the group consisting of platinum, palladium, gold and rhodium, or a substance formed by thermal decomposition and selected from the group consisting of platinum, palladium and gold, said barrier layer being capable of enhancing sensitivity to isobutane gas relative to other gases.

U.S. Pat. No. 5,293,866 issued to Padula Mar. 15, 1994 provides a description of an indicator device which can be attached to a standard oxygen flow meter is disclosed. The indicator device described in the Padula patent has a rod along which a pointer can be moved and locked into position. The pointer in the Padula patent can be set at the oxygen flow level prescribed by the physician as indicated by the scale on the oxygen flow meter. If the oxygen flow level, as described in the Padula patent, is changed or if oxygen is discontinued for any period of time, the attendant can then set the oxygen flow to the prescribed level by controlling the valve on the oxygen flow meter so that the float, which indicates oxygen flowing liters per minute is positioned opposite the position of the pointer. The foregoing mechanism recited in the Padula patent prevents erroneous or improper setting of oxygen flow levels to patients after interruption or change of oxygen flow level, which can be dangerous, and life threatening.

To the extent that the foregoing references are relevant to the present invention, they are herein specifically incorporated by reference. Where temperatures are given, they are in degrees C. unless otherwise indicated. Pressure measurements are reported in KPa. Percentages and ratios given herein are by weight unless otherwise indicated. Measurements herein are stated in degrees of approximation and where appropriate the word "about" may be inserted before any measurement.

SUMMARY OF THE INVENTION

The present invention describes a personal gas supply delivery system comprising:
   a first conduit, for when in use receiving a supply of a gas at a first pressure from a first gas supply line,
   said first conduit connected with a gas flow alarm, said gas flow alarm for when in use for determining an instantaneous difference in the pressure or volume of the gas per unit of time and the volume of the effluent gas per unit of time,
   a second conduit connected with said gas flow alarm, for when in use receiving the supply of gas through said gas flow alarm,
   said first conduit having a first connector, for when in use providing a detachable airtight seal with a compatible connector on the gas supply line, said first connector located distally from said gas flow alarm, and
   said second conduit having a second connector, for when in use providing a detachable airtight seal with a compatible connector on a second gas supply line, said second connector located distally from said gas flow alarm.

The present invention further describes a personal gas supply delivery system comprising:
   a moisturizing vessel, for when in use, having the capability to contain a liquid to provide a source of moisture to increase the amount of moisture in a gas passing through the liquid,
   said moisturizing vessel having a first opening for receiving an influent gas,
   said moisturizing vessel having a second opening for an effluent gas,
   a first conduit connected with said second opening, said first conduit for when in use, for receiving the effluent gas,
   a gas flow alarm connected with said first conduit, and
   a second conduit connected with said gas flow alarm, said second conduit in fluid communication with said first conduit,
said gas flow alarm for determining the instantaneous pressure differential of the influent gas and the effluent gas.

Yet a further embodiment of the invention is a personal gas supply delivery system comprising:
   a moisturizing vessel, for when in use, having the capability to contain a liquid to provide a source of moisture to increase the amount of moisture in a gas passing through the liquid,
   said moisturizing vessel having a first opening for receiving an influent gas,
   said moisturizing vessel having a second opening for an effluent gas,
   a first conduit connected with said second opening, said first conduit for when in use, for receiving the effluent gas,
   a gas flow alarm connected with said first conduit, and
   a second conduit connected with said gas flow alarm, said second conduit in fluid communication with said first conduit,
   said gas flow alarm for determining an instantaneous difference in the volume of the influent gas per unit of time and the volume of the effluent gas per unit of time.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DETAILED DESCRIPTION OF THE INVENTION

Figure 1:
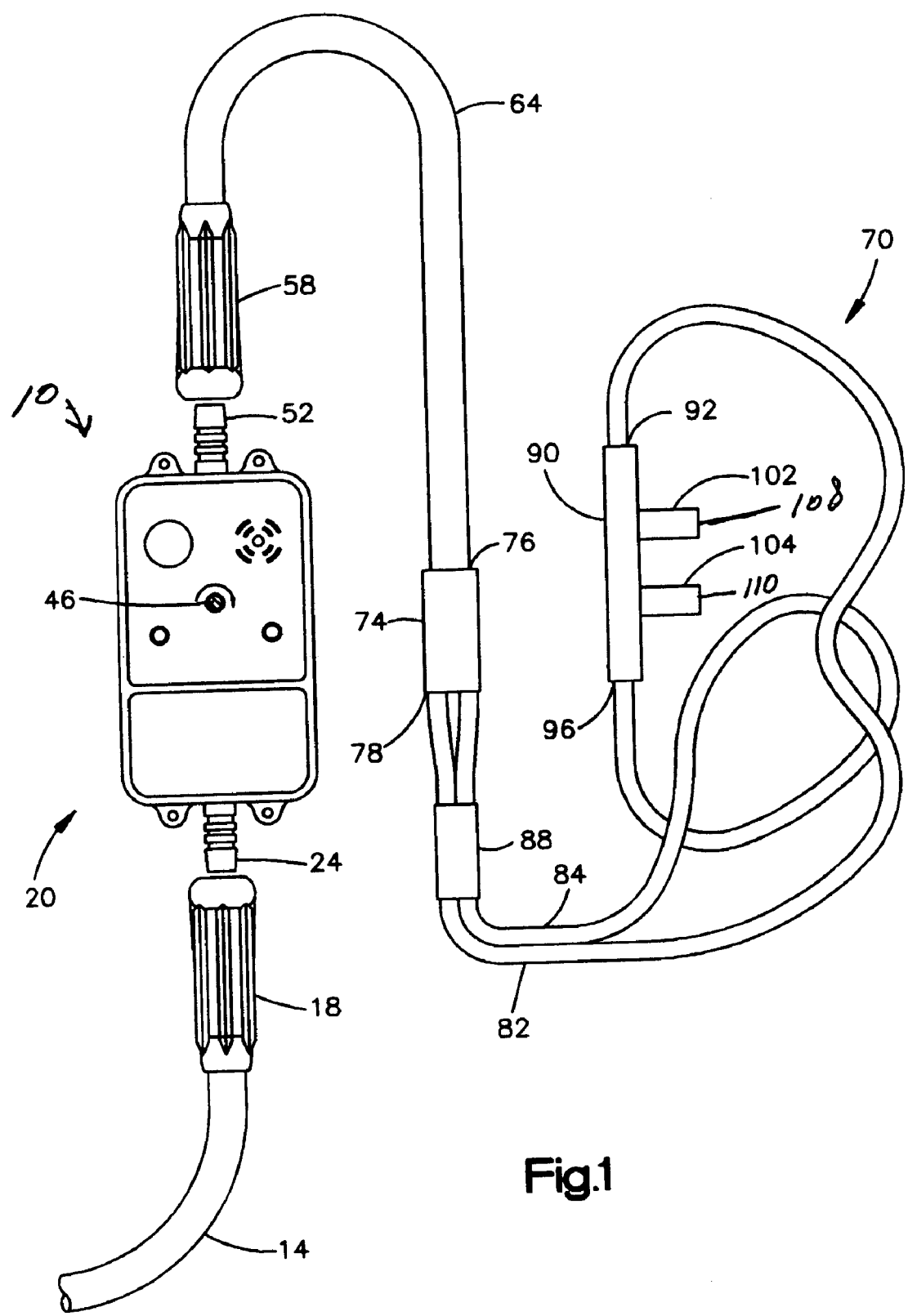
FIG. 1 is a frontal perspective of a finished product embodiment according to the invention.

As best seen in FIG. 1 there is a finished product embodiment according to the present invention. A personal gas delivery system 10 includes a hollow flexible tubing 14. The hollow flexible tubing 14 is conveniently any sufficiently flexible tubing to permit movement without undue risk of crimping, cracking or other damage, which may interrupt the flow of a medical gas.

A suggested hollow flexible tubing 14 is Tygon tubing available from Saint-Gobain Performance Plastics Corporation PO Box 3660, Akron, Ohio 44309. Saint-Gobain may be reached toll free at 800-798-1544 and direct at 330-798-9240 or at http://www.tygon.com/.

The hollow flexible tubing 14 is permanently terminated by a hollow tubing connector 18. The hollow tubing connector 18 is conveniently forced into a nipple connector 24 extending from the gas flow alarm 20. The hollow tubing connector 18 is conveniently detachable from the nipple connector 24 through moderate hand pressure with a twisting motion. The hollow flexible tubing 14 is in fluid communication with the hollow tubing connector 18, and the nipple connector 24.

In a typical usage, it is not necessary to employ any lubricant to ensure an airtight fit of the hollow flexible tubing connector 18 to the nipple connector 24. Similarly, there is no need for caulking or adhesive to ensure an airtight fit of the hollow tubing connector 18 to the nipple connector 24.

The nipple connector 24 is made of a rigid plastic such as polyvinylchloride, polycarbonate. The nipple connector 24 may also be made of other suitable rigid plastic materials.

The nipple connector 24 is affixed at the opposite end thereof with a gas flow alarm 20. The point of attachment of the gas flow alarm 20 to the hollow tubing connector 18 is by a nipple connector 24 extending from the gas flow alarm 20. The nipple connector 24 is more particularly shown in FIG. 2. The hollow tubing connector 18 is in fluid communication with the first nipple connector 24.

The gas flow alarm 20 is one, which is suitable for low flow rates and relatively low pressures. Typically, the gas flow alarm 20 is capable of determining the instantaneous pressure differential of a supply of a medical gas in the range of about 0.005 KPa to about 200 Kpa preferably 0.013 KPa to about 150 Kpa, (the equivalent of 0.05 in/$H_2O$ as a low end and 550 in/$H_2O$), above the ambient atmospheric pressure. That is, the supply of a medical gas will be determined by a flow rate approximately equal to the ambient pressure with ambient at see level being 101 KPa (14.7 pounds per square inch).

The low flow rates and relatively low pressures are utilized because the system is designed to provide a supplement of a medical gas to a patient rather than forcing the gas into the lungs of the patient. The system will work to provide accurate data at elevations from slightly below sea level to above about three thousand meters (minus 200 feet mean sea level to about ten thousand feet).

Figure 4:
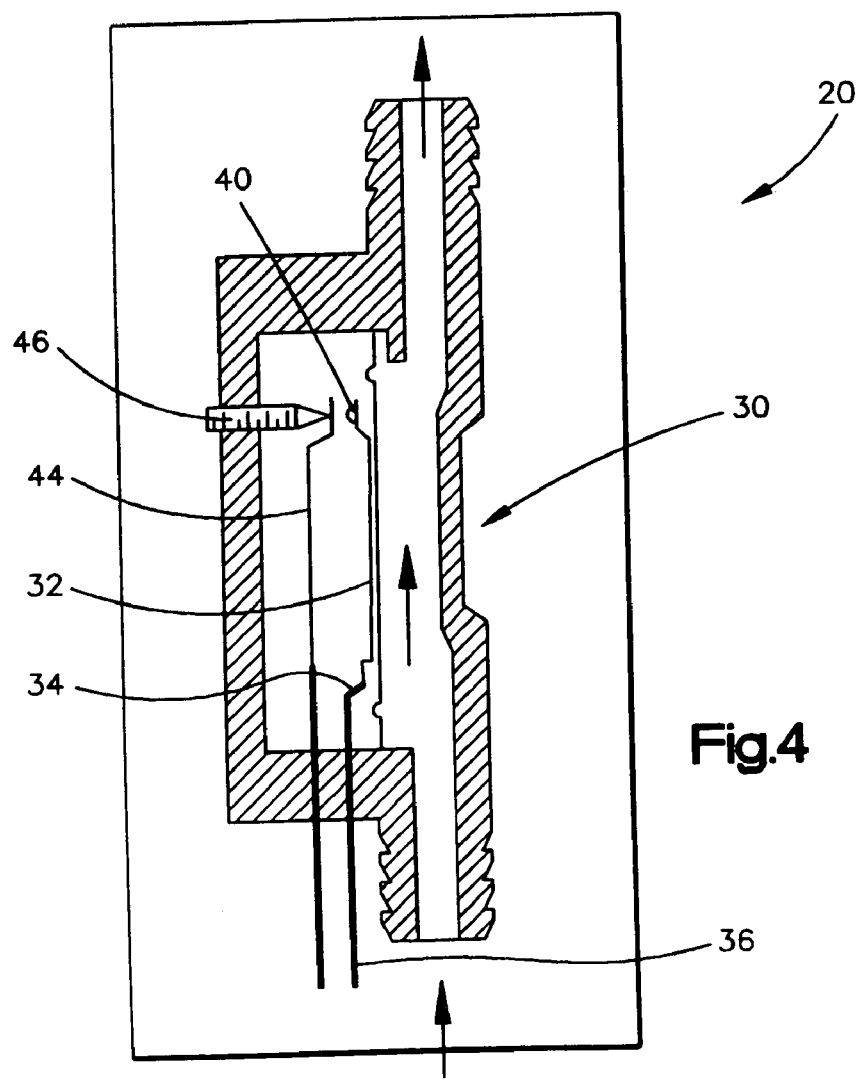
FIG. 4 is a partial sectional view of the alarm according to the invention.

As best seen in FIG. 4 a switch 30 suitable for use in the gas flow alarm 20 has a flexible metallic reed 32. The flexible metallic reed 32 is connected at an end 34 to an electrical terminal 36. The electrical terminal 36 is connected to a low voltage current source. The flexible metallic reed 32 has second end 40. The second end 40 of the flexible metallic reed 32 contacts a second electrical terminal 44 to complete an electrical circuit. The flexible metallic reed 32 is sufficiently flexible enough to permit a relatively low flow (consequently low pressure) of a medical gas to displace (break) the second end 40 of the flexible metallic reed 32 away from the second electrical terminal 44 thereby interrupting the electrical circuit. The direction of the flow of the medical gas according to the present invention is shown in FIG. 4 by the arrow. A set screw 46 permits the switch 30 to be variably set to accommodate different sensitivities for the gas flow alarm 20. The set screw 46 impinges on the second electrical terminal 44 to place the second electrical terminal 44 in closer proximity to the second end 40 thereby making the switch 30 more sensitive to gas flow.

Suitable gas flow alarms 20 are described in U.S. Pat. No. 3,133,997 to Greene issued May 19, 1964 that describes a fluid-pressure activated switch. Pressure activated switches are described in the MPL publication available at mpl@pressureswitch.com from Micro Pneumatic Logic Inc., 555 SW 12 th Avenue Pompano Beach, Fla. 33069. Further disclosures of pressure activated switches are found at World Magnetics 810 Hastings Street Traverse City, Mich. 49686, telephone: 231-946-3800 and fax: 231-946-0274 and located on the web at http://www.worldmagnetics.com The gas flow alarms described in U.S. Pat. No. 3,133,997 to Greene, the MPL publication from Micro Pneumatic Logic Inc., and the World Magnetics are specifically incorporated herein by reference.

Figure 2:
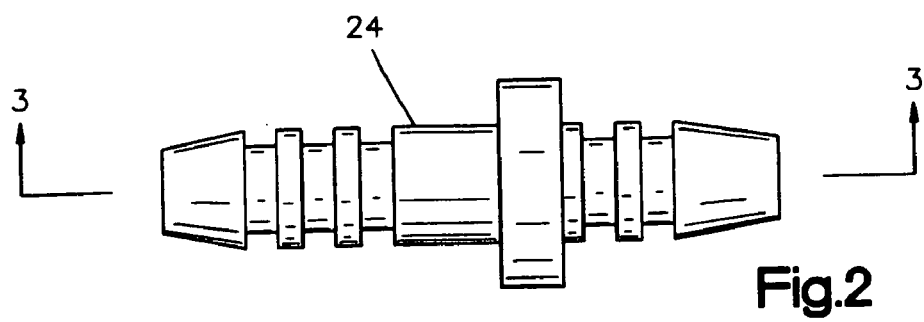
FIG. 2 is a frontal perspective of a part of the finished product embodiment according to the invention.
Figure 3:
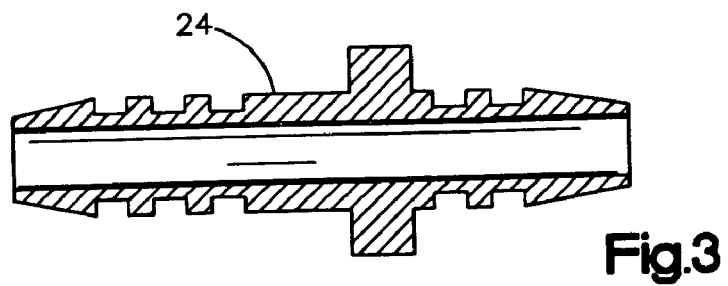
FIG. 3 is a sectional view of a part of the finished product embodiment according to the invention taken along line 3—3.

As best seen in FIG. 2, the gas flow alarm 20 has protruding from it a second nipple connector 52. The second nipple connector 52 is similar in construction and design to the first nipple connector 24. The second nipple connector 52 is in fluid communication with the gas flow alarm 20.

A second hollow tubing connector 58 plastic such as PVC or polycarbonate. The design and construction of the second hollow tubing connector 58 is similar to that of the hollow tubing connector 18. The second hollow tubing connector 58 is in fluid communication with the second nipple connector 52 and accordingly is in fluid communication with the gas flow alarm 20.

The second hollow tubing connector 58 is connected with a second hollow flexible tubing 64. The second tubing connector 58 is conveniently forced into the second nipple connector 52. The hollow flexible tubing 64 is in fluid communication with the hollow tubing connector 58. The second hollow tubing connector 58 is conveniently detachable from the second nipple connector 52 through moderate hand pressure with a twisting motion.

The suggested hollow flexible tubing 64 is Tygon tubing available form the same source as the hollow flexible tubing 14. As with the hollow connector tubing 18, the hollow tubing connector 58 it is not necessary to employ any lubricant to ensure an airtight fit of the hollow tubing connector 58 to the nipple connector 52. Similarly, there is no need for caulking or adhesive to ensure an airtight fit of the hollow connector tubing 58 to the nipple connector 52.

The second hollow flexible tubing 64 is connected with a gas distributive device 70. The point of the connection of the hollow flexible tubing 64 is connected with a gas distributive device 70 is with a unitary to binary connector 74. The unitary to binary connector 74 connects at the unitary opening 76 to the hollow flexible tubing 64. The unitary to binary connector 74 is in fluid communication with the hollow flexible tubing 64. The second hollow flexible tubing 64 is permanently connected to the unitary to binary connector 74.

The unitary to binary connector 74 has a binary opening 78 at the end distal from the unitary opening 76. The binary opening 78 is in fluid communication with the unitary opening 76 and accordingly with the second hollow flexible tubing 64.

The unitary to binary connector 74 is formed of a hollow tube 82 and a second hollow tube 84. The first hollow tube 82 and the second hollow tube 84 are conveniently obtained as a co-extruded material. The first hollow tube 82 and the second hollow tube 84 are typically formed from a flexible material such as the previously discussed Tygon tubing. The first hollow tube 82 and the second hollow tube 84 are each separately in fluid communication with the binary opening 78.

A clip 88 is conveniently utilized to maintain the first hollow tube 82 and the second hollow tube 84 in close proximity. The clip 88 is a "C" shaped hard plastic into which the first hollow tube 82 and the second hollow tube 84 are inserted and held in place in the interior curvature of the "C" by pressure fitting. The clip 88 is with moderate effort slideably engaged on the outer surface of the first hollow tube 82 and the second hollow tube 84.

The first hollow tube 82 connects with nasal cannula 90 via a first nasal cannula fitting 92. The second hollow tube 84 with a second nasal cannula fitting 96. The first nasal cannula fitting 92 is in fluid communication with first hollow tube 82. The nasal cannula 90 is connected with a second nasal cannula fitting 96. The second nasal cannula fitting 96 is in fluid communication with second hollow tube 84.

The first nasal cannula fitting 92 and the second nasal cannula fitting 96 are a part of the hollow nasal cannula tube 90. The first nasal cannula fitting 92 and the second nasal cannula fitting 96 are both in fluid communication with the hollow nasal cannula tube 90.

The nasal cannula tube 90 has protruding from it a pair of spaced apart nasal fittings 102 and 104. The spaced apart nasal fittings 102 and 104 are in fluid communication with the hollow nasal cannula tube 90.

The spaced apart nasal fittings 102 and 104 have nasal orifices 108 and 110. The nasal orifices 108 and 110 permit the flow of a medical gas out of the nasal cannula tube 90 to the nostrils of a patient in need of the medical gas.

To avoid accidental disconnection and the resultant false alarms, it is suggested that each of the hollow flexible tubing 14 and the hollow flexible tubing 64 be from 25 centimeters to 2 meters, preferably 30 centimeters to one meter in length.

The personal gas delivery system 10 permits the hollow flexible tubing 14 to receive a medical gas, such as oxygen, from a medical gas supply source (not shown). The hollow flexible tubing 14 receives the medical gas allowing the flow of a medical gas to the hollow tubing connector 18.

The medical gas passes through the hollow tubing connector 18 in an uninterrupted flow to the gas flow alarm 20. The medical gas passes through the gas flow alarm 20. If the flow rate of the medical gas is below a predetermined point then the alarm is activated.

The activation of the alarm may be by an audible signal to alert at least the patient that the flow rate of the medical gas is below a predetermined point. As the patient may be suffering from a hearing impairment it is also possible to utilize a visible light to alert the patient that the flow rate of the medical gas is below a predetermined point.

As the patient may be patient may be suffering from a hearing impairment and a lack of visual acuity it is also possible to utilize a vibratory mechanism to alert the patient that the flow rate of the medical gas has fallen below a predetermined point. The vibratory mechanism is least favored, as it requires an external power source to avoid premature discharge of the batteries.

Each of the alarms, audible, visual and vibratory has disadvantages. As noted the audible alarm is of limited value with a hearing impaired patient. The light activated alarm requires a sighted patient and is of little use when the patient is sleeping or when the alarm light is hidden beneath a blanket or other covering. Similarly, the vibratory mechanism as an alarm is of limited value when the patient is sleeping and may be covered with a blanket which may absorb the vibrations which are intended to alert the patient that the flow rate of the medical gas has fallen below a predetermined point.

If the system is otherwise operating properly the medical gas flows through the gas flow alarm 20, through the second nipple connector 52 and into the second hollow tubing connector 58. The medical gas then flows from the second hollow tubing connector 58, into hollow flexible tubing 64, and from there into the gas distributive device 70.

The purpose of having the flow of medical gas divided into two flow paths is important in the present invention. As the gas flow alarm 20 is upstream from the nasal cannula tube 90 it possible for any of the components from the gas flow alarm 20 downstream to become non-functional, e.g. blocked. For example, one of the pair of spaced apart nasal fittings 102 and 104 may become blocked because of mucous in the opening the affected nasal fitting.

Similarly, one of the first hollow tube 82 and a second hollow tube 84 may be crushed or otherwise blocked. As the present invention permits having the flow of medical gas divided into two flow paths at least some of the medical gas passing through one of the hollow tubes will likely reach the patient. In any other case, the alarm 20 may be fully functional and the patient would still not receive an adequate supply of the medical gas.

Figure 6:
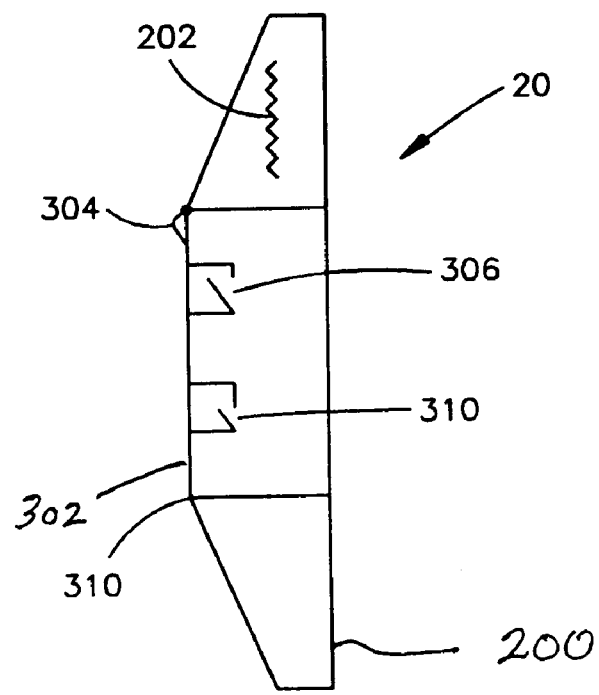
FIG. 6 is an anterior view of a part of the finished product embodiment according to the invention.

Thus, as an additional feature to the alarm aspect of the present invention is a transmitter 200. The transmitter 200 is shown in FIG. 6. The transmitter 200, when connected with the gas flow alarm 20, transmits the fact that the flow rate of the medical gas has fallen below a predetermined point to a remote receiving location such as a nursing station. The transmitter 200 is any conventional low power device that does not interfere with the operation of the overall system. The transmitter 200 transmits a radio signal through an antenna 202.

Figure 5:
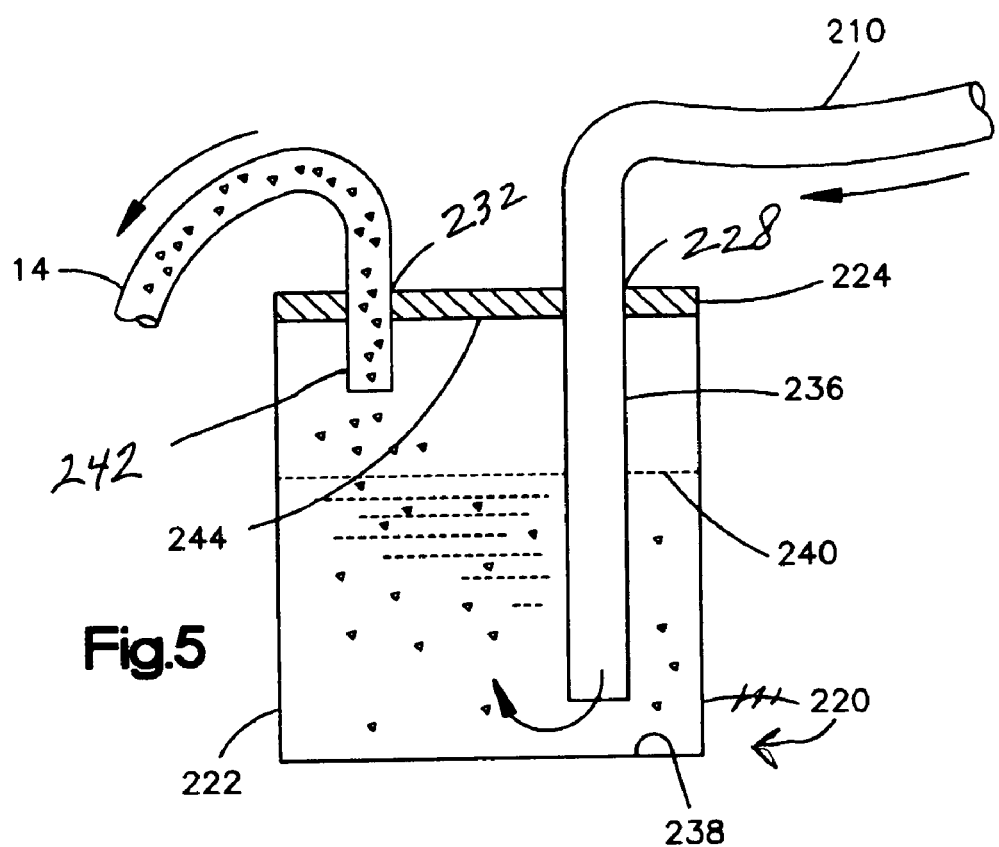
FIG. 5 is a frontal perspective of a part of the finished product embodiment according to the invention.

A second embodiment of the present invention employs the feature of moisturizing a medical gas to be supplied to the patient. As best seen in FIG. 5, is a medical gas supply line 210. The medical gas supply line 210 is connected with a humidifying device 220. The humidifying vessel 220 comprises a humidifying container (or moisturizing vessel) 222 and a humidifying container cap 224.

The humidifying container 222 has a screw sealing mechanism at its upper opening. The humidifying container cap 224 has a screw sealing mechanism. The humidifying container cap 224 has a screw sealing mechanism is mated to the screw sealing mechanism of the humidifying container 222. The humidifying container cap 224 has extending there through a first opening 228. The humidifying container cap 224 has extending there through a second opening 232.

A gas delivery conduit 236 extends through the first opening 228 in the humidifying container cap 224. The gas delivery conduit 236 extends into the humidifying container 222, when the humidifying container cap 224 is screwed onto the humidifying container 222, to a point just above the humidifying container lower surface 238. In practice, the gas delivery conduit 236 will be below the level of the humidifying liquid in the humidifying container 222.

A gas receiving conduit 242 extends through the second opening 232 in the humidifying container cap 224. The gas receiving conduit 242, extends into the humidifying container 222, when the humidifying container cap 224 is screwed onto the humidifying container 222, to a point just below the bottom 244 of the humidifying container cap 224. When the personal gas delivery system 10 is in operation the gas receiving conduit 242 will not extend below the level of the humidifying liquid in the humidifying container 222.

A medical gas is introduced to the delivery conduit 236 and into the humidifying container 222. The humidifying container 222 is filed to a point about 2 centimeters below its top with distilled water. The gas delivery conduit 236 is below the level of the humidifying liquid in the humidifying container 222. The medical gas from the gas delivery conduit 236 is humidified in the humidifying container 222.

The gas receiving conduit 242 takes up the humidified medical gas. The arrow in FIG. 5 shows the direction of gas flow. The medical gas then passes through the gas flow alarm 20 as previously described.

A third embodiment of the invention is shown in FIG. 6. In the last embodiment of he invention there is disclosed a switch 300 for the gas flow alarm 20. The gas flow alarm 20 has an anterior surface 302. Located on the anterior surface 302 is a light 304 for alerting the patient that the gas flow alarm 20 has detected a low pressure or low flow rate of the medical gas.

To allow the patient to be confident that the gas flow alarm 20 is operating properly there is an alarm test switch 306. A second switch on the anterior surface of the gas flow alarm 20 is an on off switch 310. The on off switch 310 is located on the anterior surface 302 of the gas flow alarm 20. The gas flow alarm 20, when activated will provide a continuous signal until the alarm is reset, or the alarm is inactivated, or the batteries are depleted.

Accordingly, there is a need to manually reset the alarm when the alarm is activated. When the medical gas supply is intentionally interrupted such as to replace the gas supply, to provide services to the patient such as bathing the patient, or to replenish the humidifying liquid 242 in the humidifying container 222, it is desirable to turn off the gas flow alarm 20.

Accordingly, the gas flow alarm 20 may also provide an on off switch (or a test feature) 310.

Although the above description and accompanying drawings relate to a specific preferred embodiment as presently contemplated by the inventors, it will be understood that the invention in its broad aspect includes mechanical and functional equivalents of the elements described and illustrated.

What is claimed is:

1. A personal gas supply delivery system comprising:
a moisturizing vessel, for when in use, having the capability to contain a liquid to provide a source of moisture to increase the amount of moisture in a gas passing through the liquid,
said moisturizing vessel having a first opening for receiving an influent gas,
said moisturizing vessel having a second opening for an effluent gas,
a first conduit connected with said second opening, said first conduit for when in use, for receiving the effluent gas,
a gas flow alarm connected with said first conduit, and
a second conduit connected with said gas flow alarm, said second conduit in fluid communication with said first conduit,
said gas flow alarm for determining the instantaneous pressure or flow volume of the influent gas and the effluent gas;
said second conduit has a length such that the gas flow alarm, when is use by a recipient of the effluent gas, is proximate to the recipient of the effluent gas, provided further that said personal gas supply delivery system has a gas flow alarm reset or test feature having an anterior surface where a switch to operate the alarm reset or the test feature is located substantially flush with or below the said anterior surface.

2. A personal gas supply delivery system comprising:
a moisturizing vessel, for when in use, having the capability to contain a liquid to provide a source of moisture to increase the amount of moisture in a gas passing through the liquid,
said moisturizing vessel having a first opening for receiving an influent gas,
said moisturizing vessel having a second opening for an effluent gas,
a first conduit connected with said second opening, said first conduit for when in use, for receiving the effluent gas,
a gas flow alarm connected with said first conduit, and
a second conduit connected with said gas flow alarm, said second conduit in fluid communication with said first conduit,
said second conduit is unitary and connecting with a binary nasal cannula;
said gas flow alarm for determining an instantaneous difference in the pressure or volume of the influent gas per unit of time and the volume of the effluent gas per unit of time,
provided further that said personal gas supply delivery system has a gas flow alarm reset or test feature having an anterior surface where a switch to operate the alarm reset or the test feature is located substantially flush with or below the said anterior surface.

3. The personal gas supply delivery system according to claim 1 wherein the gas flow alarm is set to alert a second person by means of a transmitter and a receiver that the pressure or the volume per unit of time of the influent gas and the effluent gas has met at least one predetermined setting.

4. The personal gas supply delivery system according to claim 3 wherein the second person is alerted by the receiver.

* * * * *